United States Patent [19]

Schwierz et al.

[11] 4,455,667
[45] Jun. 19, 1984

[54] RADIATION DIAGNOSTIC DEVICE FOR GENERATING TOMOGRAPHIC IMAGES

[75] Inventors: Günter Schwierz; Rudolf Schittenhelm; Günter Schmitt, all of Erlangen; Edgar Tschunt, Rathsberg, all of Fed. Rep. of Germany

[73] Assignee: Siemens Aktiengesellschaft, Berlin & Munich, Fed. Rep. of Germany

[21] Appl. No.: 236,525

[22] Filed: Feb. 20, 1981

Related U.S. Application Data

[63] Continuation-in-part of Ser. No. 058,464, Jul. 18, 1979, Pat. No. 4,297,582.

[30] Foreign Application Priority Data

Aug. 9, 1978 [DE] Fed. Rep. of Germany ....... 2834934

[51] Int. Cl.³ .............................................. G03B 41/16
[52] U.S. Cl. .......................................... 378/4; 378/17; 378/20
[58] Field of Search ................................. 378/17, 20, 4

[56] References Cited

U.S. PATENT DOCUMENTS 3,973,126  8/1976  Redington ............................ 378/17

*Primary Examiner*—Craig E. Church
*Attorney, Agent, or Firm*—Hill, Van Santen, Steadman & Simpson

[57] ABSTRACT

In the exemplary embodiments a layer is to be scanned which is generally parallel to the longitudinal axis of the patient support. For example, a radiation source and a radiation receiver may be rotated in an arc about a rotational axis which lies perpendicular to the longitudinal axis of the patient support to scan a layer area in such a way that the scanned layer within the exposure subject is traversed exclusively along beam paths each of which is crossed along its entire length in the subject by a multitude of other beam paths.

5 Claims, 9 Drawing Figures

RADIATION DIAGNOSTIC DEVICE FOR GENERATING TOMOGRAPHIC IMAGES

CROSS-REFERENCE TO RELATED APPLICATION

The present application is a continuation-in-part of Ser. No. 58,464 filed July 18, 1979, now U.S. Pat. No. 4,297,582 issued Oct. 27, 1981.

BACKGROUND OF THE INVENTION

The invention relates to a radiation diagnostic device for generating tomographic images of an exposure subject with a positioning table or patient support, with a measuring arrangement for irradiation of the exposure subject from various directions comprising a radiation source which emits radiation beams penetrating the layer to be investigated, the dimension of said radiation beams perpendicular to the layer plane being equal to the thickness of the layer, and a radiation receiver which supplies electrical output signals according to the measured radiation intensity, and with a computer connected to the radiation receiver for the calculation of the attenuation values of specific image points of the irradiated body layer from the output signals of the radiation receiver.

Radiation diagnostic devices of this type, so-called computer tomographs, are known in which the measuring arrangement is rotatable about an axis which lies in the longitudinal direction of the positioning table or patient support. In such apparatus, the x-ray source generates a fan-shaped x-ray beam which is received by a series of detectors which form the radiation receiver. If the measuring arrangement, whose x-ray source lies on the one side and whose radiation receiver lies on the other side of the positioning table is rotated around the exposure subject lying on the positioning table, then it is possible to calculate and visually reproduce the attenuation values of predetermined points of the layer of the exposure subject to be examined from output signals of the radiation receiver thereby generated. With the known radiation diagnostic devices of the type initially cited, because of the position of the rotational axis of the measuring arrangement, it is only possible to generate tomographic images of layers of the exposure subject which lie transverse to the longitudinal axis of the exposure subject and transverse to the longitudinal direction of the positioning table.

SUMMARY OF THE INVENTION

The object of the invention is to design a computer tomograph in such manner that images of layers which lie in the longitudinal direction of the exposure subject, and, thus, of the positioning table can be generated with it.

This object is inventively achieved in that the rotational axis of the radiation beam intersects the longitudinal direction of the positioning table, in particular is arranged perpendicular thereto, in such manner that the scanned layer area in which the exposure subject lies is penetrated exclusively by rays in which each beam path is crossed over its entire length in the subject by many other beam paths and the angular range for the scanning rays seen from each subject point may be smaller than $\pi$ radians (180°). The invention proceeds on the basis that, with a layer scanning device of the type initially cited, a computational image reconstruction is possible when the scanned layer range of unknown ray attenuation is penetrated exclusively by rays in which each beam path is crossed over its entire length by many other beam paths, and that it is possible to meet this requirement by means of a suitable arrangement of the rotational axis of the measuring arrangement even in layer exposures in which the layer examined lies in the longitudinal direction of the patient positioning table.

A practical embodiment of the invention comprises an arrangement wherein the measuring arrangement is carried on a turntable for adjusting the position of the scanned layer, and the turntable is rotatable on a pedestal around a horizontal rotational axis as well as around the rotational axis lying perpendicular to the longitudinal direction of the positioning table; and that the positioning table is seated on a second pedestal and can be adjusted in height. Given this embodiment, it is possible to examine layers of the exposure subject which lie in the longitudinal direction of the positioning table and have any desired angle to the positioning table as well as any desired interval from it.

A further embodiment of the invention provides that the radiation source and the radiation receiver are fastened to a respective one of a pair of booms which encompass the positioning table, and that the radiation source has a beam shaping diaphragm allocated to it which is moved during a scanning process to progressively change the extent of a fan-shaped beam in such manner that the marginal rays of the rays serving for the image calculation of the fan-shaped beam always extend tangential to two convex curves, preferably circular arcs, whose midpoints lie beyond the area covered by the scanning beam. Given this embodiment, extended longitudinal layers in the body to be examined can be represented. If the positioning table is rotatably arranged around a vertical axis so that it can be brought into a position in which the rotational axis of the radiation beam lies parallel to the longitudinal axis of the positioning table or coincides with such longitudinal axis, then standard computer tomograms of layers which proceed perpendicularly through the exposure subject can also be produced with such a device.

In the following, the invention is described in greater detail on the basis of exemplary embodiments illustrated in the accompanying sheets of drawings; and other objects, features and advantages will be apparent from this detailed disclosure and from the appended claims.

DETAILED DESCRIPTION

Figure 1:
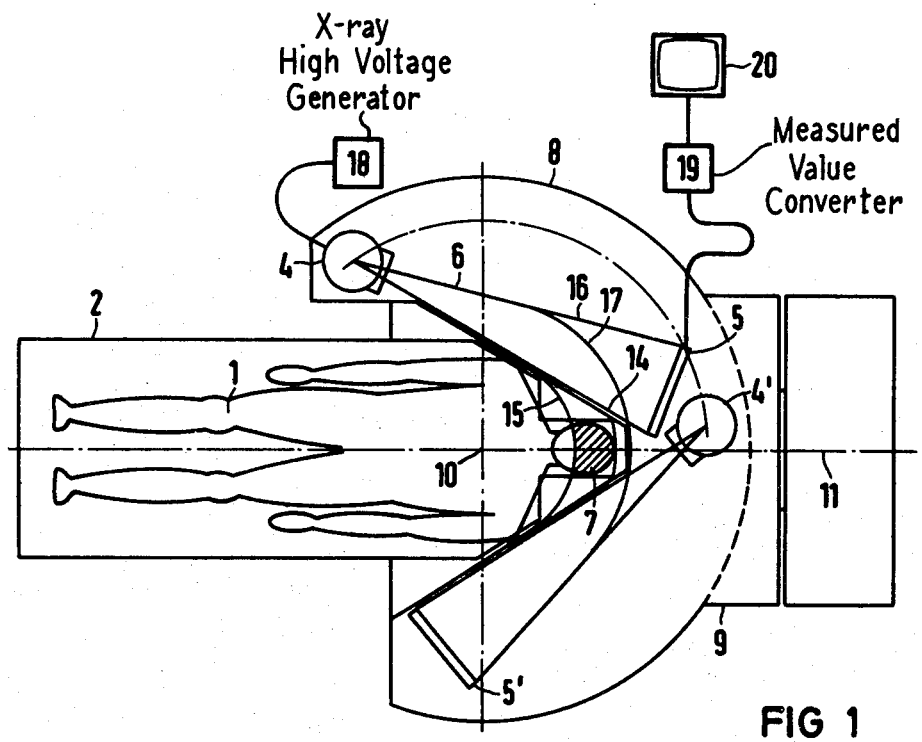
FIG. 1 is a diagrammatic top plan view of a radiation diagnostic device according to the invention.
Figure 2:
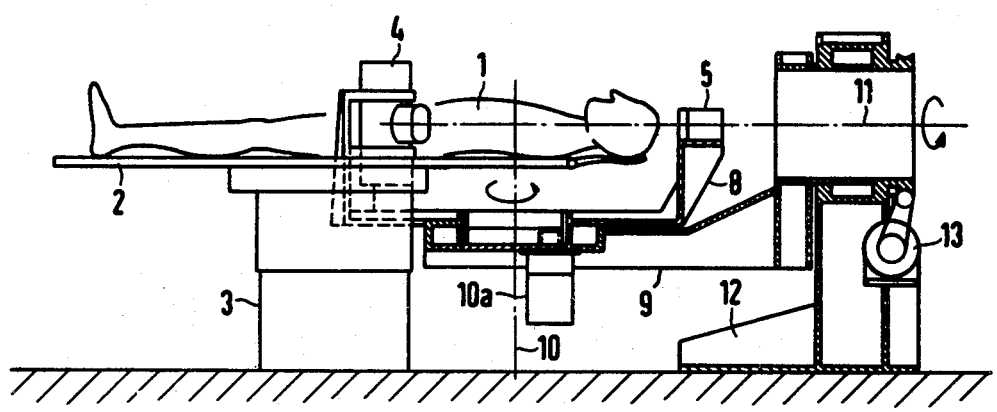
FIG. 2 is a side view of the radiation diagnostic device according to FIG. 1, with certain parts shown in vertical section.

A patient 1 lying on a positioning table or patient support 2 is illustrated in FIGS. 1 and 2. The positioning table 2 is mounted on a pedestal 3 so as to be adjustable in height and movable in the direction of its length. For examining the patient 1, namely the patient's head in the example, a measuring arrangement with an x-ray source 4 and a radiation receiver 5 is provided. The radiation receiver 5 consists of a series of individual detectors, for example in the order of more than 100 detectors, which are struck by a fan-shaped x-ray beam 6. In its dimension perpendicular to the examined layer 7 of the patient 1, the extent of the x-ray beam 6 is equal to the thickness of the layer. The measuring arrangement 4, 5 is fastened to a turntable 8 which is rotatable on a carrier 9 about an axis 10 by means of a motor 10a (FIG. 2). The carrier 9 is in turn connected with a footing 12 and rotatable around a horizontal axis 11. A motor 13 is provided for the rotation of the carrier 9 about horizontal axis 11.

FIG. 1 is intended to show that the measuring arrangement can be brought from an initial position with the x-ray source at 4 and the radiation receiver at 5 into a final position which is designated with 4' for the x-ray source and with 5' for the radiation receiver by turning the turntable 8 about axis 10. During this rotation about axis 10, the one limiting ray path 14 of the x-ray beam 6 revolves on a circular arc 15 and the other limiting ray path 16 revolves on circular arc 17. The rotational axis 10 is located relative to the positioning table or patient support 2 in such a manner that the scanned layer of the patient's head (indicated by shading in FIG. 1), i.e. the layer area 7 of unknown beam attenuation to be examined, is exclusively penetrated along beam paths in the patient 1 each of which is crossed over its entire length, by a multitude of other beam paths during the rotation of the turntable 8. The angular range as seen from each subject point about which the x-ray source 4 is moved may be significantly smaller than $\pi$ radians; and preferably lies between $\pi$ and $\frac{1}{2}\pi$ radians. This requirement is met when the circular arc 17 lies beyond the head of the patient 1. During a scanning process, i.e. during the movement of the measuring arrangement from the initial position at 4, 5 into the final position designated by means of the symbols 4', 5', the x-ray source 4 which is fed by an x-ray generator 18 can be pulsed at periodic intervals. By so doing, a plurality of groups of output signals are obtained from the radiation receiver 5 corresponding to the number of pulses, such output signals being supplied to a computer or measured value converter 19. The computer 19, because of the fact that each beam path in the layer area 7 is crossed, along its entire length, by a plurality of other beam paths, is in a position to calculate the beam attenuation coefficients of predetermined array of points covering the layer area 7 from the output signals of the radiation receiver 5. Thereby, it is possible, by means of a corresponding control of a visual display 20, to reproduce an image of the layer area 7 after the scanning.

In the illustrated initial position of the turntable 8 with the measuring arrangement at 4, 5, FIG. 1, a layer, namely, the layer area 7, is scanned which lies parallel to the positioning table 2. By turning the turntable 8 about the horizontal axis 11, it is possible to also examine layers whose planes intersect with the plane of the positioning table 2. Because of the height adjustability of the positioning table 2, the examined layers can respectively have any desired height level.

In the exemplary embodiment, the examined layer area 7 lies between the two circular arcs 15 and 17, FIG. 1. It is important that the circular arc 17 proceed beyond the examined layer area, i.e. the scalp of the patient 1, for only in that case is the requirement met that each beam path in the layer of unknown beam attenuation is crossed, along its entire length in the examination subject, by a multitude of other beam paths. In that case in which the circular arc 17 would proceed through the head of the patient, the layer area beyond the circular arc 17 would be penetrated by beam paths which have no intersection points in the above sense. In this case, therefore, no reconstruction of an image over the entire extent of the layer area 7 would be possible.

Figure 3:
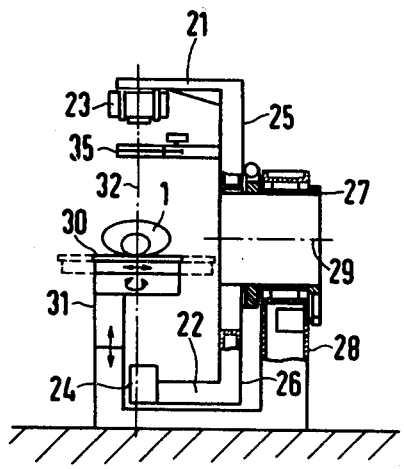
FIGS. 3 through 5 show various diagrammatic views of another embodiment of a radiation diagnostic device according to the invention.
Figure 4:
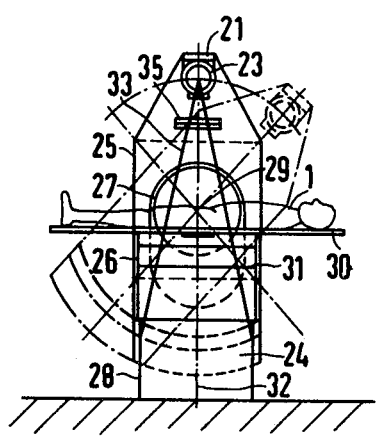
Figure 5:
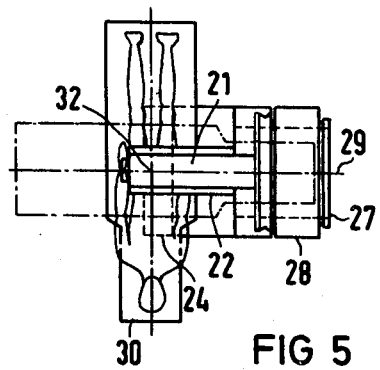

The device according to FIGS. 3 through 5 exhibits two booms 21 and 22. An x-ray tube 23 is fastened to the boom 21 and a radiation receiver 24 which likewise consists of a series of individual detectors is fastened to the boom 22. The booms 21 and 22, which encompass the positioning table 30, are connected by arms 25, 26 with a hollow shaft 27 which is rotatably journalled for rotation about an axis 29 on a pedestal 28. The positioning table 30 for the patient 1 is arranged displaceable in all directions on a carrier 31. The carrier 31 together with the positioning table 30 is height adjustable. Further, the positioning table 30 can be rotated with respect to the carrier 31 about a vertical axis 32.

In the illustrated position, any desired longitudinal layer of the patient 1 to be examined can be selected by means of a lateral displacement of the positioning table 30. In the case shown in FIG. 3, the selected longitudinal layer passes approximately through the axis of symmetry of the patient 1. If, for scanning the patient 1, the measuring arrangement 23, 24 is rotated around the axis 29 according to FIG. 6, then the x-ray beam 33, according to FIG. 6, scans the longitudinal layer 34 of the patient 1. A primary ray diaphragm 35 is adjusted during this scanning process in such manner that the marginal rays 33-1 and 33-2 of the fan-shaped ray beam 33 in the layer to be examined always proceed tangential to two arcs 36, 37 whose centers of curvature lie beyond the area to be scanned by the x-ray beam 33. In the two final positions 33' and 33" of this x-ray beam illustrated in FIG. 6, the beam is constricted to a narrow beam by the ray diaphragm 35, whereas in the illustrated midposition the beam has its greatest width. By means of this adjustment of the ray diaphragm 35, one obtains, so to speak, a breathing x-ray beam, and the condition is met that the scanned layer area 34 be penetrated exclusively by beam paths in which each beam path is intersected, along its entire length in the subject, by a multitude of other beam paths.

Figure 7:
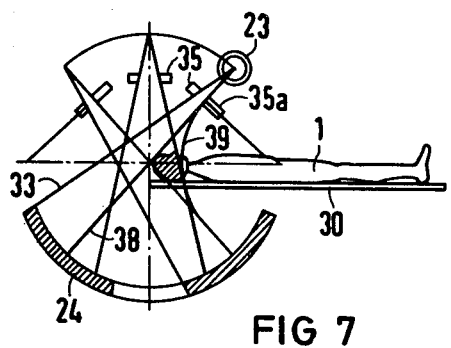

FIG. 7 shows a position in which the head of the patient is to be imaged. To this end, only the half of the ray diaphragm 35, namely the half 35a is adjusted so that the marginal beam 38 always proceeds tangential to one circular arc 39 which limits the examined layer in the head of the patient 1.

Figure 8:
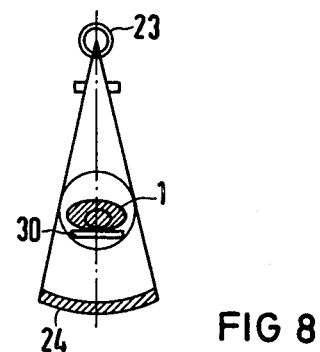

If the positioning table 30 is rotated by 90° from the position illustrated in FIGS. 3 through 7, then, in accordance with FIG. 8, a computer tomogram of a transverse layer of the patient 1 can be represented in a known manner.

For the sake of clarity, the x-ray generator as well as the computer and the visual display are not illustrated in FIGS. 3 through 8.

The exemplary embodiments according to FIGS. 1 and 2 are based on the theory that, for imaging a body layer with the assistance of a computer tomograph, projections from a scanning angular range which is smaller than 180° are sufficient when the scanning ensues in such manner that the center of rotation (in German the "Drehpunkt") of the x-ray beam lies beyond this x-ray beam. In the framework of the invention, it is not necessary in the example according to FIGS. 3 through 8 to also move the radiation receiver 24. It is possible to employ a radiation receiver of such an extent that it is always struck by x-rays and to use only those detectors of the radiation receiver which respectively receive the rays of the x-ray beam in each scanning position thereof. Further, it is conceivable to also displace the x-ray source linearly or to dispense with a mechanical movement of the x-ray tube when an x-ray tube is employed in which an electronic movement of the x-ray beam is possible in the sense of a rotation of its central beam.

In the framework of the invention, for imaging layers which lie oblique to the longitudinal direction of the patient, it is possible to arrange the rotational axis of the x-ray beam with an angle with respect to this longitudinal direction deviating from 90°, whereby it thereby also intersects this longitudinal direction, particularly the patient longitudinal axis.

It will be apparent that many modifications and variations may be effected without departing from the scope of the novel concepts and teachings of the present invention.

SUPPLEMENTARY DISCUSSION

Figure 6:
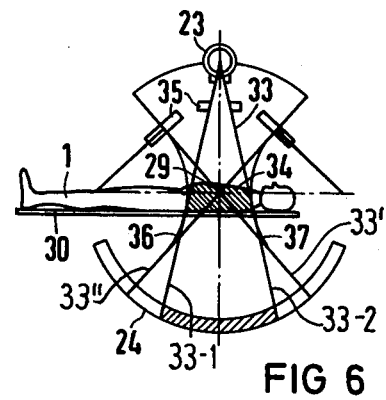
FIGS. 6 through 9 are schematic illustrations for explaining the manner of functioning of the device according to FIGS. 3 through 5.
Figure 9:
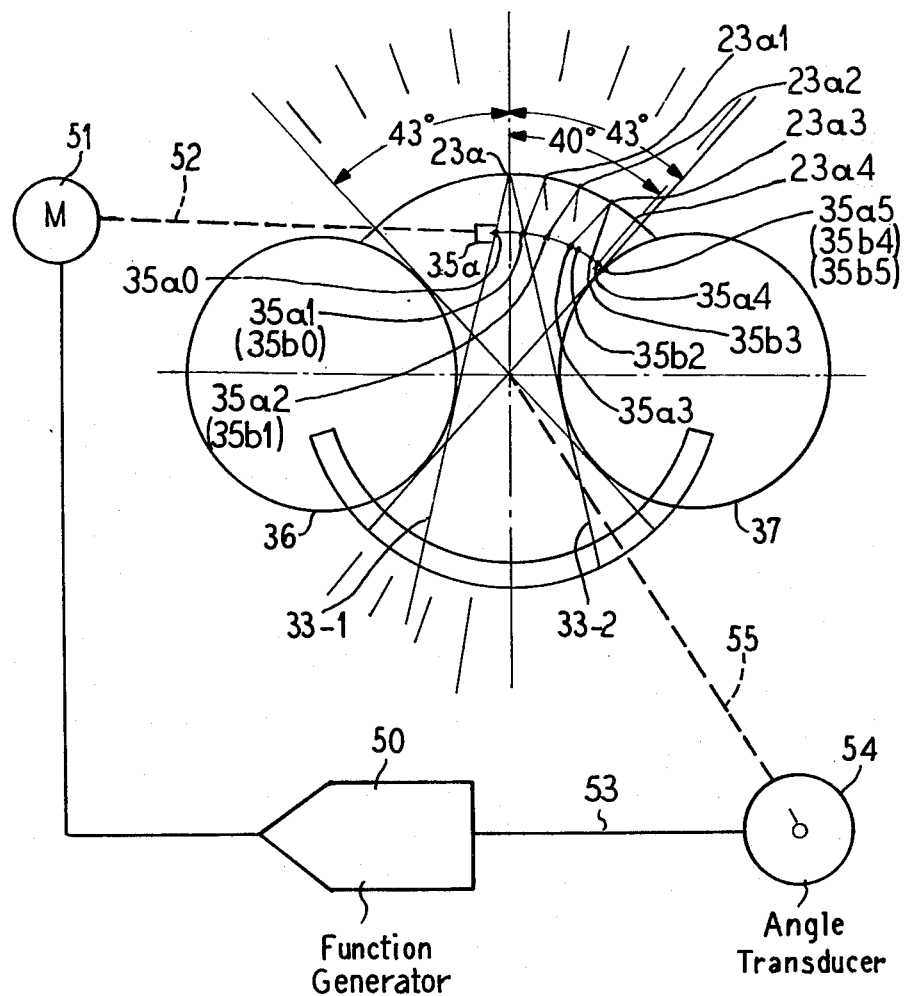

Referring to FIG. 6, for example, the two sections of diaphragm 35 may be designated 35a and 35b. FIG. 9 illustrates the positions of diaphragm section 35a for angular displacements of focus 23a of x-ray source 23. Thus, position 23a1 represents the position of the focus of x-ray source 23 when the x-ray source has been rotated ten degrees clockwise from the position shown in FIG. 6. Position 23a2 shows rotation through twenty degrees clockwise from the position of FIG. 6 and position 23a3 shows the position of focus 23a after thirty degrees of clockwise rotation from the position of FIG. 6. Focal position 23a4 represents the position after forty degrees of clockwise rotation.

With respect to focus position 23a1 in FIG. 9, marginal ray 33-1 is to extend tangent to arc 36 and marginal ray 33-2 is to extend tangent to arc 37. It will be apparent that this defines the required positions for diaphragm sections 35a and 35b when the x-ray source 23 is rotated ten degrees clockwise from the position of FIG. 6. By way of example, the position of diaphragm section 35a for the ten degree focal position 23a1 has been designated 35a1 in FIG. 9. Similarly, the required positions of diaphragm section 35a for the twenty degree and thirty degree focal positions 23a2 and 23a3 are designated 35a2 and 35a3 in FIG. 9, while the position for diaphragm section 35a for the forty degree focal position 23a4 is designated 35a4 in FIG. 9.

Referring to FIG. 6, the final extreme clockwise position of focus 23 of x-ray tube 23 is designated 23a5, and the corresponding position of diaphragm section 35a is indicated at 35a5, the positions of the diaphragm sections 35a and 35b in the extreme clockwise position defining a very thin x-ray beam 33" as previously described which is tangent to both of arcs 36 and 37. In FIG. 6, the corresponding initial position of the diaphragm section 35a is designated 35a0.

Referring to FIG. 9, it will be observed that the successive positions of diaphragm section 35a for the successive ten degree angular increments are relatively uniformly spaced. It is, of course, completely apparent to those skilled in the art that the diaphragm section 35a can be successively positioned at points 35a1 through 35a4 as a function of the angular movement of the x-ray source 23.

Referring to FIG. 9, it will be apparent that the marginal rays 33-2 in the successive focal positions 23a, and 23a1 through 23a5 define successive positions of the diaphragm section 35b which are entirely similar to the position such as 35a1 through 35a5. Thus, the position (35b0) essentially corresponds to position 35a1. The ten degree position (35b1) essentially corresponds to point 35a2 in FIG. 9. The twenty degree position 35b2 is slightly distinct from point 35a3 and has actually been indicated in FIG. 9. Similarly the thirty degree position 35b3 is somewhat distinct from point 35a4 and has actually been indicated in FIG. 9. The forty degree position for diaphragm section 35b (35b4) and the final position of this diaphragm section 35b (35b5) are similar to the extreme clockwise position provided by the position of diaphragm section 35b indicated at 35" in FIG. 6. Position 35b5 has been generally indicated in FIG. 6 for the sake of completeness.

Of course, referrring to FIG. 6, the motion of diaphragm section 35b from the position shown at 35b0 to the extreme counterclockwise position corresponding to position 35b' of the diaphragm section is entirely analogous to the clockwise motion of diaphragm section 35a in moving to its extreme clockwise position as indicated at 35a" in FIG. 6. Furthermore, the motion of diaphragm section 35a in the counterclockwise direction to its extreme position indicated at 35a' in FIG. 6 corresponds to the clockwise motion of diaphragm section 35b as has just been described.

As will be clear to those skilled in the art, the mechanization of the desired movement of diaphragm sections 35a and 35b as described with respect to FIG. 9 is a routine matter. For example, it is only necessary to measure the respective scanning position of the x-ray source 23, and to generate the corresponding required electrical signals for controlling the positions of the respective diaphragm sections 35a and 35b. It is, of course, common in the radiology art to electrically control primary diaphragm plates, and to utilize function generators to produce desired electrical functions. Accordingly, for the sake of diagrammatic indication in FIG. 9, an arbitrary function generator 50 has been indicated as electrically coupled with a motor 51 which controls the position of the diaphragm section 35a by means of a mechanical coupling indicated at 52. The input at 53 to the function generator 50 is shown as being supplied by angle transducer 54 which is coupled as indicated at 55 with the angular rotation of the x-ray source 23, FIG. 6. The symbol for the arbitrary function generator 50 is taken from the *McGraw-Hill Encyclopedia of Science and Technology*, Vol. 1 (1971), FIG. 14 at page 402, the arbitrary function generator being explained with reference to FIG. 10a at page 399 of said Vol. 1. As indicated at page 401 of said Vol. 1, an operational relay may respond to analog signals (for example representing the angular position of x-ray source 23) for switching from one function generator circuit to another should this be desired, for example to utilize the function generator 50 to drive a motor coupled with the diaphragm section 35b during counterclockwise movement of the x-ray source from the position shown in FIG. 6.

We claim as our invention:

1. A radiation diagnostic device for generating tomographic images of an exposure subject with a positioning table for supporting an exposure subject so as to lie generally parallel to a horizontally disposed longitudinal axis of the table, with a measuring arrangement for the irradiation of the exposure subject from various directions comprising a radiation source which emits a radiation beam penetrating the body layer to be examined, and a radiation receiver which supplies electric output signals corresponding to the measured radiation intensity, and with a measured value converter connected to the radiation receiver for calculating the attenuation values of specific iamge points of the irradiated body layer from the output signals of the radiation receiver, characterized in scanning means providing for rotation of the radiation beam about a rotational axis which extends transversely to the longitudinal axis of the positioning table, in such, manner that a layer area which is to correspond to the body layer to be examined is scanned by being penetrated exclusively by beams directed along beam paths each of which is crossed, along its entire length in the subject, by a multitude of other beam paths, said scanning means being further characterized in that the rotational axis (10) of the radiation beam (6) lies outside of the layer area covered by the radiation beam (6).

2. A radiation diagnostic device according to claim 1, characterized in that the angular range for the scanning beams as seen from each subject point lies between $\pi$ and $\frac{1}{2}\pi$ radians.

3. A radiation diagnostic device according to claim 1, characterized in that said scanning means comprises a turntable (8) mounting the measuring arrangement (4, 5), and a pedestal (9, 12) mounting the turntable (8) for rotation about a horizontal axis (11) which extends parallel to the longitudinal axis of the positioning table for the adjustment of the position of the scanned layer area (7), said scanning means providing for rotation of the turntable (8) about a rotational axis (10) lying perpendicular to the longitudinal axis of the positioning table (2) to effect scanning of said layer area (7).

4. A radiation diagnostic device according to claim 1, characterized in that said scanning means comprises a first boom (21) mounting the radiation source (23) and a second boom (22) mounting the radiation receiver (24), the booms (21, 22) encompassing the positioning table (30); and in that the radiation source (23) has a diaphragm (35) allocated to it which, during the scanning process, is moved in such manner that a marginal ray of the fan-shaped radiation beam (33) in the layer area to be examined and serving for the image calculation always are directed tangentially a two convex curves whose center of curvature lies beyond the area covered by the radiation beam (33).

5. A radiation diagnostic device according to claim 4, characterized in that the positioning table (30) is rotatable about a vertical axis (32) so that it can be brought into a position in which the rotational axis (29) of the radiation beam (33) lies parallel to the longitudinal axis of the positioning table (30).

* * * * *